US009897569B2

(12) United States Patent
Katz et al.

(10) Patent No.: US 9,897,569 B2
(45) Date of Patent: Feb. 20, 2018

(54) CIRCUITS, DEVICES AND SENSORS FOR FLUID DETECTION

(75) Inventors: Howard Edan Katz, Owings Mill, MD (US); Patrick N. Breysse, Los Angeles, CA (US); Bal Mukund Dhar, Baltimore, MD (US); Noah Jonathan Tremblay, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 26 days.

(21) Appl. No.: 13/809,134

(22) PCT Filed: Jul. 8, 2011

(86) PCT No.: PCT/US2011/043393
§ 371 (c)(1),
(2), (4) Date: Jan. 8, 2013

(87) PCT Pub. No.: WO2012/006546
PCT Pub. Date: Jan. 12, 2012

(65) Prior Publication Data
US 2013/0115136 A1     May 9, 2013

Related U.S. Application Data

(60) Provisional application No. 61/362,474, filed on Jul. 8, 2010.

(51) Int. Cl.
*G01N 27/414*     (2006.01)
*G01N 27/00*     (2006.01)
(Continued)

(52) U.S. Cl.
CPC ....... *G01N 27/4148* (2013.01); *H01L 27/088* (2013.01); *H01L 27/283* (2013.01);
(Continued)

(58) Field of Classification Search
CPC . G01N 27/4148; H01L 27/088; H01L 27/283; H01L 51/0036; H01L 51/0043; H01L 51/0053; H01L 51/0068
(Continued)

(56) References Cited

U.S. PATENT DOCUMENTS

| 4,322,680 A | 3/1982 | Janata et al. |
| 4,397,714 A | 8/1983 | Janata et al. |

(Continued)

FOREIGN PATENT DOCUMENTS

EP     1736760 A2     12/2006

OTHER PUBLICATIONS

Bartic, Carmen, and Gustaaf Borghs. "Organic thin-film transistors as transducers for (bio) analytical applications." Analytical and bioanalytical chemistry 384.2 (2006): 354-365.*

(Continued)

*Primary Examiner* — Robert Eom
(74) *Attorney, Agent, or Firm* — Venable LLP; Henry J. Daley (57) ABSTRACT

An electronic device includes a first field effect transistor that includes a first gate electrode, a first drain electrode, and a first source electrode; a second field effect transistor that includes a second gate electrode, a second drain electrode, and a second source electrode, the first and second gate electrodes being at least one of electrically connected or integral, and the first and second source electrodes being at least one of electrically connected or integral; an input electrode electrically connected to the first and second gate electrodes; and an output electrode electrically connected to the first and second source electrodes. The first field effect transistor also includes a first semiconductor material. The second field effect transistor further also incudes a second semiconductor material. At least one of the first semicon- (Continued)

ductor material and second semiconductor material has a surface that can be exposed to a fluid and changes an electrical property thereof while being exposed to the fluid.

13 Claims, 11 Drawing Sheets (51) Int. Cl.
*H01L 27/098* (2006.01)
*H01L 27/28* (2006.01)
*H01L 27/088* (2006.01)
*H01L 51/00* (2006.01)

(52) U.S. Cl.
CPC ...... *H01L 51/0036* (2013.01); *H01L 51/0043* (2013.01); *H01L 51/0053* (2013.01); *H01L 51/0068* (2013.01)

(58) Field of Classification Search
USPC .................................................. 257/252, 253
See application file for complete search history.

(56) References Cited

U.S. PATENT DOCUMENTS

| | | | |
|---|---|---|---|
| 5,045,285 A | 9/1991 | Kolesar, Jr. | |
| 6,661,299 B2 * | 12/2003 | Dodabalapur | G01N 27/4141 257/252 |
| 6,948,388 B1 * | 10/2005 | Clayton et al. | 73/862.68 |
| 2005/0053524 A1 | 3/2005 | Keersmaecker et al. | |
| 2009/0127589 A1 * | 5/2009 | Rothberg et al. | 257/253 |

OTHER PUBLICATIONS

Derycke, V., et al. "Carbon nanotube inter-and intramolecular logic gates." Nano Letters 1.9 (2001): 453-456.*
Novak, J. P., et al. "Nerve agent detection using networks of single-walled carbon nanotubes." Applied physics letters 83.19 (2003): 4026-4028.*
International Search Report and Written Opinion for PCT/US2011/043393.
Anthopoulos, *Appl. Phys. Lett.* 91, 113513 (2007).
Assadi et al., *Synthetic Metals* 37, 123-130 (1990).
Bao et al., *J. Appl. Phys. Lett.* 69, 4108 (1996).
Campbell et al., *Appl. Phys. Lett.* 95, 263302 (2009).
Dhar et al., *Mater. Sci. Eng.* R (Dec. 2010).
Dhar, et al., *Electron. Lett.* 46, 1335-1336 (Sep. 2010).
DiBenedetto et al., *Adv Mater* 21, 1407-1433 (2009).
Feldman et al., *Accounts Chem Res* 41, 1731-1741 (2008).
Fiorido et al., *Sensor. Actuat. B—Chem.* 151, 77-82 (Oct. 2010).
Guo et al., *Nat Nanotechnol* 3, 163-167 (2008).
Guo et al., *Adv. Mater.* 22, 4427-4447 (2010).
Harris et al. *J Phys Chem C* 111, 17947-17951 (2007).
Heederik et al., *Environ. Health Perspect.* 115, 298-302 (2007).
Hsu et al., *IEEE T Electron Dev* 58, 910-917 (Mar. 2011).
Huang et al. *J. Mater. Chem.* vol. 20 2644 (Nov. 2009).
Jung et al., *Adv. Funct. Mater.* 20, 2930-2944 (2010).
Jung et al., *ACS Nano* (2011).
Jung et al., *Chem. Mater.* 21, 94-101 (2009).
Jung et al., *Chem. Mater.* 23, 568-582 (Oct. 2010).
Letizia et al., *Adv Funct Mater* 20, 50-58 (Dec. 2010).
Locklin et al., *Anal Bioanal Chem* 384, 336-342 (2006).
Roberts et al. *P Natl Acad Sci Usa* 105, 12134-12139 (2008).
Roberts et al., *Org Electron* 10, 377-383 (2009).
Someya et al., *Adv. Mater.* 22, 3799-3811 (2010).
Someya et al., *Nano Lett* 3, 877-881 (2003).
Someya et al. *P Natl Acad Sci Usa* 101, 9966-9970 (2004).
Thorne, P. *Environ. Health Perspect.* 115, 296-297 (2007).
Yang et al. *Angew. Chem. Int. Ed.* vol. 49 2114-2138 (Feb. 2010).
Zheng et al., *J. Amer. Chem. Soc.* 132, 5394-5404 (Jan. 2010).

* cited by examiner

CIRCUITS, DEVICES AND SENSORS FOR FLUID DETECTION

CROSS-REFERENCE OF RELATED APPLICATION

This application is a U.S. national stage application under 35 U.S.C. § 371 of PCT/US2011/043393, filed on Jul. 8, 2011, which claims priority to U.S. Provisional Application No. 61/362,474 filed on Jul. 8, 2010, the entire contents of which are hereby incorporated by reference.

This invention was made with government support under ES 07141, awarded by the National Institute of Environmental Health Sciences Training Program; 0730926, awarded by the National Science Foundation; and FA 9550-09-1-0259, awarded by the Department of Defense, AFOSR. The Government has certain rights in the invention.

BACKGROUND

1. Field of Invention

The field of the currently claimed embodiments of this invention relates to electronic sensors, devices and circuits, and more particularly to electronic sensors, devices and circuits for sensing fluids.

2. Discussion of Related Art

Organic conductors and semiconductors have been harnessed for the detection of an enormous variety of molecular vapors (Someya, T., Dodabalapur, A., Huang, J., See, K. C. & Katz, H. E. Adv. Mater. 22, 3799-3811 (2010); Locklin, J. & Bao, Z. *Anal Bioanal Chem* 384, 336-342 (2006); Yang, W. et al. in Angew. Chem. Int. Ed. Vol. 49 2114-2138 (2010)), small molecules in solution (Locklin, J. & Bao, Z. *Anal Bioanal Chem* 384, 336-342 (2006); Roberts, M. E. et al. *P Natl Acad Sci Usa* 105, 12134-12139 (2008)), biomolecules (Roberts, M. E. et al. *P Natl Acad Sci Usa* 105, 12134-12139 (2008); Guo, X., Gorodetsky, A. A., Hone, J., Barton, J. K. & Nuckolls, C. *Nat Nanotechnol* 3, 163-167 (2008)), electromagnetic radiation (Campbell, I. H., Crone, B. K., *Appl. Phys. Lett.* 95, 263302 (2009)), temperature (Letizia, J. A., Rivnay, J., Facchetti, A., Ratner, M. A. & Marks, T. J. *Adv Funct Mater* 20, 50-58 (2010)), and mechanical force (Hsu, Y.-J., Jia, Z. & Kymissis, I. *Ieee T Electron Dev* 58, 910-917 (2011); Someya, T. et al. *P Natl Acad Sci Usa* 101, 9966-9970 (2004)). The transduction mechanism to an electronic signal can be a perturbation of the charge carrier distribution in response to chemical binding, reaction, absorption, or adsorption; a change in carrier energy levels, a change in dipole orientation, and/or a change in the carrier transport pathway between two electrodes (Someya, T., Dodabalapur, A., Huang, J., See, K. C. & Katz, H. E. Adv. Mater. 22, 3799-3811 (2010)). A rich variety of organic and carbon-based materials have been enlisted for this application, including conjugated organic molecules and polymers (Roberts, M. E., Mannsfeld, S. C. B., Stoltenberg, R. M. & Bao, Z. *Org Electron* 10, 377-383 (2009)), carbon nanotubes and graphene (Guo, X., Gorodetsky, A. A., Hone, J., Barton, J. K. & Nuckolls, C. *Nat Nanotechnol* 3, 163-167 (2008); Huang, J. et al. in J. Mater. Chem. Vol. 20 2644 (2010); Harris, K. D. et al. J Phys Chem C 111, 17947-17951 (2007); Someya, T., Small, J., Kim, P., Nuckolls, C. & Yardley, J. Nano Lett 3, 877-881 (2003); Feldman, A. K., Steigerwald, M. L., Guo, X. & Nuckolls, C. *Accounts Chem Res* 41, 1731-1741 (2008)), and polymer composites (DiBenedetto, S. A., Facchetti, A., Ratner, M. A. & Marks, T. J. *Adv Mater* 21, 1407-1433 (2009)). However, the architecture aspect of these devices is still in the first stage, namely, so-called chemiresistors, chemicapacitors, and organic field-effect transistors (OFETs). To take advantage of the true potential of these devices, it is desirable to integrate these sensors into the information medium of electronics, which is binary. Digital or binary language is very powerful in that it allows engineers to interface basic organic sensors with existing electronics components to ultimately produce usable products. However, sensitivity and selectivity are two main areas that demand improvement for organic electronic sensors. Therefore, there remains a need for improved electronic sensors, devices and circuits for sensing fluids.

SUMMARY

An electronic device according to an embodiment of the current invention includes a first field effect transistor that includes a first gate electrode, a first drain electrode, and a first source electrode; a second field effect transistor that includes a second gate electrode, a second drain electrode, and a second source electrode, the first and second gate electrodes being at least one of electrically connected or integral, and the first and second source electrodes being at least one of electrically connected or integral; an input electrode electrically connected to the first and second gate electrodes; and an output electrode electrically connected to the first and second source electrodes. The first field effect transistor also includes a first semiconductor material. The second field effect transistor further also includes a second semiconductor material. At least one of the first semiconductor material and second semiconductor material has a surface that can be exposed to a fluid and changes an electrical property thereof while being exposed to the fluid.

An electronic sensor according to an embodiment of the current invention includes a power source, a semiconductor component electrically connected to the power source, the semiconductor component including a semiconducting material; an input electrode electrically connected to the semiconductor component; and an output electrode electrically connected to the semiconductor component. The electronic sensor provides a first output voltage when a first input voltage has a value that is below a range of transition voltages. The electronic sensor also provides a second output voltage when a second input voltage has a value that is above the range of transition voltages. The first output voltage is greater than the second output voltage, and the semiconductor material is at least partially exposed such that a fluid of interest can be brought into contact with the semiconductor material to cause a change in the range of transition voltages.

An electronic circuit according to an embodiment of the current invention includes a plurality of electrically connected electronic components, wherein at least one of the plurality of electrically connected electronic components is an inverter. The inverter includes a first field effect transistor that includes a first gate electrode, a first drain electrode, and a first source electrode; a second field effect transistor that includes a second gate electrode, a second drain electrode, and a second source electrode, the first and second gate electrodes being at least one of electrically connected or integral, and the first and second source electrodes being at least one of electrically connected or integral; an input electrode electrically connected to the first and second gate electrodes; and an output electrode electrically connected to the first and second source electrodes. The first field effect transistor further includes a first semiconductor material. The second field effect transistor further comprises a second semiconductor material. At least one of the first semiconductor material and second semiconductor material has a surface that can be exposed to a fluid, and at least one of the first semiconductor material and second semiconductor material changes an electrical property thereof while being exposed to the fluid.

An electronic circuit for a fluid sensor according to an embodiment of the current invention includes an electronic component that includes a first material section and a second material section, an input electrode electrically connected to the electronic component, and an output electrode electrically connected to the electronic component. Each of the first and second materials has a surface that can be exposed to a fluid. Each of the first and second materials changes an electrical property upon being exposed to the fluid to register a change in an output to the output electrode indicative of a presence of the fluid.

BRIEF DESCRIPTION OF THE DRAWINGS

Further objectives and advantages will become apparent from a consideration of the description, drawings, and examples.

FIG. 9A-9D provide data for an example of CMOS inverter behavior upon exposure to isopropylamine according to an embodiment of the current invention.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

One aspect of some embodiments of the current invention enables sensors to enhance sensitivity and selectivity from two or more different materials, some of which may not be sensitive or selective enough on their own.

Figure 1A:
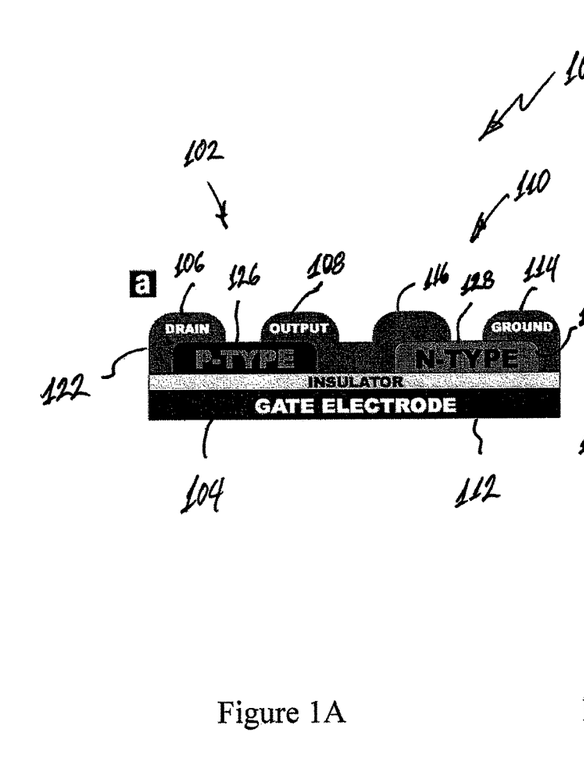
FIGS. 1A and 1B are schematic illustrations of an electronic device according to an embodiment of the current invention.
Figure 1B:
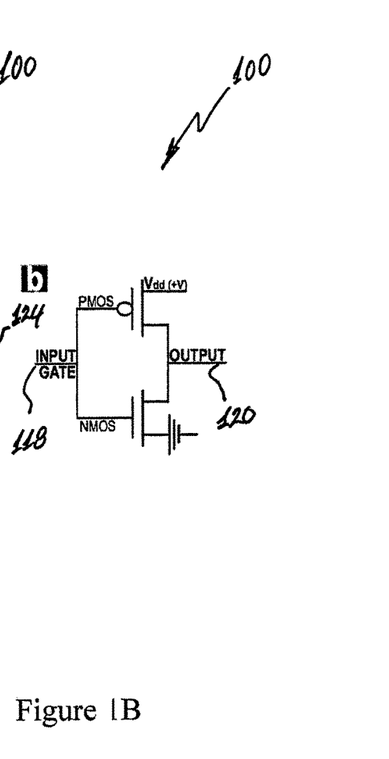
Figure 3:
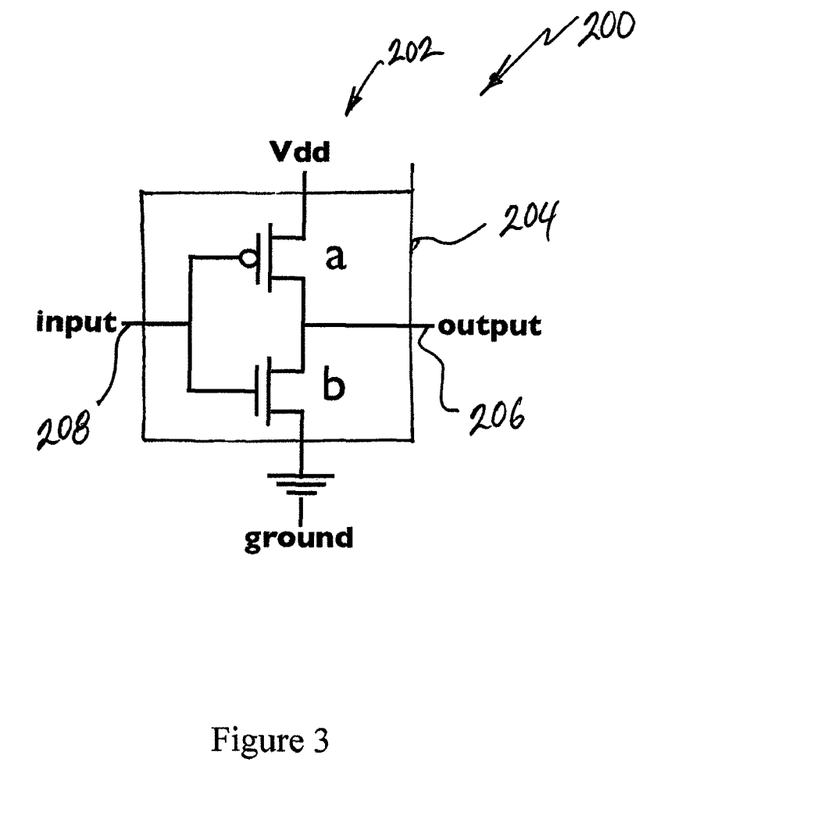
FIG. 3 is a circuit diagram to help explain concepts of another body of the current invention.

Logic gate device architectures consist of p-type and n-type transistors. Incorporating p- and n-type transistors that are sensitive to an analyte into logic gate structures can increase sensitivity and selectivity according to some embodiments of the current invention. In addition, incorporation can make data measuring, collecting, and interpretation much simpler and easier. The inverter structure (a simple NOT logic gate) is shown in FIG. 1B and FIG. 3. In the case where transistors a and b are both electrically sensitive to an analyte, the inverter is also sensitive. In the case where transistors a and b behave in synergy, the inverter structure can provide an increased sensitivity and/or selectivity. An example of a possible synergistic effect is when transistor a displays an increase in current, mobility, or threshold voltage upon analyte exposure and transistor b displays a decrease in current, mobility, or threshold voltage. Because the output of the inverter is dependent on both transistors (both materials), their opposing changes will be reflected as a summation, creating an overall heightened response compared to either transistor individually.

A fundamental idea related to sensing systems mentioned in the Background section is to move from changing current levels (e.g., in chemiresistors) or changing current levels, mobility, or threshold voltages (e.g., in OFETs) to a conversion of those signals into incremental, easily electronically distinguishable steps. Essentially, this is an analog to digital conversion. This principle has already gained some attention for electro-optical sensors (T. D. Anthopoulos, Appl. Phys. Lett. 91, 113513 (2007); Guo, Y., Yu, G. & Liu, Y. Adv. Mater. 22, 4427-4447 (2010)). The device that is most fundamental to this conversion is the simple electronic inverter based on the complementary metal-oxide-semiconductor (CMOS)-type structure (shown in FIG. 1). The CMOS inverter is the simplest 'NOT' logic gate, converting a high voltage into a zero voltage and vice-versa. The CMOS inverter structure can take advantage of the different and opposing behavior of n-type and p-type materials in OFETs according to an embodiment of the current invention. N-type materials turn on when the gate electrode is at a positive voltage relative to the channel, and p-type materials turn on when the gate electrode is negative. If both p- and n-OFETs share the same gate electrode then one OFET can allow current flow (and voltage equilibration) while the other does not. If we connect the n-type OFET to the OFF signal (ground), then an applied positive gate voltage induces current flow in the n-type organic semiconductor (OSC) and the output signal is ground or OFF. When the gate voltage is zero, the n-type OSC is no longer conductive. The zero gate voltage results in a net negative voltage across the p-type OSC when it is also connected to a positive voltage; it then allows current flow, making the output a high positive voltage (Vdd), the digital equivalent of "one". The switching voltage of a CMOS inverter is the point at which below this voltage the output approaches an externally set voltage (Vdd) and above this voltage the output is zero volts. This switching voltage can be tuned in many different ways to achieve the desired value. This includes simply changing the dimensions of the inverter electrodes. However, the switching phenomenon is not sensitive to the absolute values of the input voltages except near the switching voltage; the outputs are generally either zero or Vdd, with little variation.

Figure 2A:
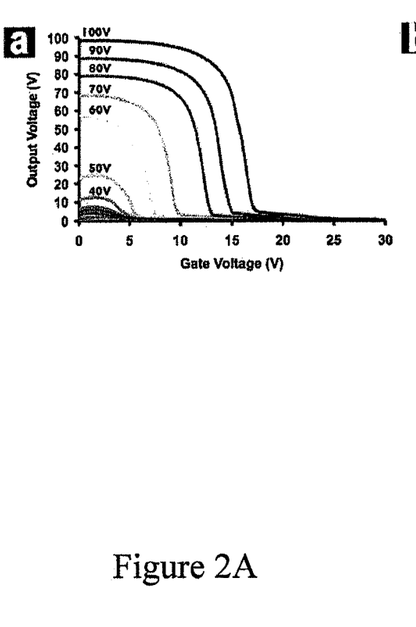
FIGS. 2A and 2B provide CMOS inverter behavior (gate voltage versus output voltage at different values of Vdd) for (a) a device made with 8-3 NTCDI and CuPC; and (b) a device made with 8-3 NTCDI and 6PTTP6.
Figure 2B:
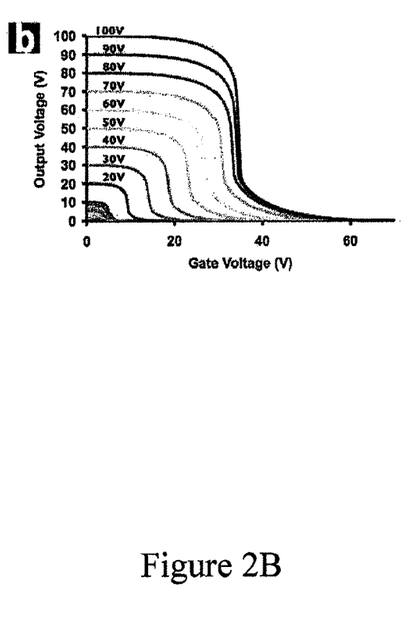

There are several factors that affect inverter behavior. The mobility and threshold voltage matching of the two OSCs used determine at which voltage and how sharply the switching can occur. The externally set voltage (Vdd) changes the absolute voltage at which the inverter will switch. This voltage affects inverters made from different OSCs differently. For example, input-output curves for inverters made from two different p-semiconductors and the same n-semiconductor are shown in FIGS. 2A-2B. (Note that the x-axes are not identical in FIGS. 2A and 2B, and are scaled for maximum distinction of the curves). Clearly, when the materials are better matched in mobility and threshold voltage, the switching occurs closer to the half-way point between zero and $V_{dd}$. This idea is the basis of our previous work using individual OFET threshold voltage tuning through charged dielectrics to shift the switching voltage (Dhar, B. M., Özgün, R., Dawidczyk, T., Andreou, A. & Katz, H. E. Mater. Sci. Eng. R (2010), doi:10.1016/j.mser.2010.11.001; Dhar, B., Ozgün, R., Jung, B., Katz, H. & Andreou, A. Electron. Lett. 46, 1335-1336 (2010)). Analytes can affect the switching voltage of inverters made from sensitive semiconductors by changing the threshold voltages and/or mobilities of either or both semiconductors. The use of this effect to generate synergistic and digital responses to amine vapors is an example of one possible application for an embodiment of the current invention. A more application-specific motivation towards development of amine-sensitive devices is the growing demand for cheap ammonia sensors for use in agriculturally intensive areas, specifically to monitor their possible associated health risks to the surrounding communities (Thorne, P. *Environ. Health Perspect.* 115, 296-297 (2007); Heederik, D., Sigsgaard, T., Thorne, P. S., Kline, J. N., Avery, R., & Bønløkke, J. H. *Environ. Health Perspect.* 115, 298-302 (2007)).

More generally, an electronic device 100 according to an embodiment of the current invention includes a first field effect transistor 102 that includes a first gate electrode 104, a first drain electrode 106, and a first source electrode 108 (See FIG. 1A). The electronic device 100 also includes second field effect transistor 110 that includes a second gate electrode 112, a second drain electrode 114, and a second source electrode 116. The first and second gate electrodes (104, 112) are electrically connected or integral as a common gate electrode. In the example of FIG. 1A, the gates electrodes 104, 112 are formed as a common, integral gate electrode. The first and second source electrodes 108, 116 are electrically connected or integral. An input electrode 118 is electrically connected to the first and second gate electrodes 104, 112 (not shown in FIG. 1A, see FIG. 1B). An output electrode 120 is electrically connected to the first and second source electrodes 108, 116. The first field effect transistor 102 further includes a first semiconductor material 122. The second field effect transistor 110 further includes a second semiconductor material 124. At least one of the first semiconductor material 122 and second semiconductor material 124 has a surface that can be exposed to a fluid, such as surface 126 or 128. At least one of the first semiconductor material 122 or the second semiconductor material 124 changes an electrical property thereof while being exposed to the fluid.

In an embodiment, each of the first semiconductor material 122 and the second semiconductor material 124 has a surface that can be exposed to the fluid such that both the first semiconductor material and the second semiconductor material changes an electrical property while being exposed to the fluid. In some embodiments, each of said first semiconductor material 122 and the second semiconductor material 124 changes an electrical property while being exposed to the fluid in a synergistic way such that an effect of exposure to the fluid is enhanced. In some embodiments, the first semiconductor material 122 can be a different material from the second semiconductor material 124. In some embodiments, the first semiconductor material 122 can be a p-type semiconductor material and the second semiconductor material 124 can be an n-type semiconductor material, for example. However, the general concepts of the current invention are not limited to this example. In other embodiments, they could both be n-type or they could both be p-type semiconductors, for example. In some embodiments, the first semiconductor material 122 and/or the second semiconductor material 124 can be an organic semiconductor material. However, the general concepts of the current invention are not limited to only organic semiconductor materials. Organic semiconductor materials could be used for the semiconductor material 122 and/or 124 in some embodiments of the current invention.

In some embodiments, the first semiconductor material 122 at least one of decreases carrier mobility and/or increases a threshold voltage upon being exposed to the fluid. In some embodiments, the second semiconductor material 124 increases carrier mobility and/or decreases a threshold voltage upon being exposed to said fluid.

In some embodiments, the fluid is a gas and/or a vapor. In some embodiments, the fluid is a liquid, a suspension and/or an emulsion. In some embodiments, the fluid includes ammonia, an amine, aza-aromatic compound with pKa>4, dihydrogen sulfide, and/or an organic thiol. In some embodiments, the fluid includes a compound with an acidic proton, or a Lewis acidic functionality. In this case, the p-type semiconductor would show increased carrier mobility/decreased threshold voltage, while the n-type semiconductor would show the opposite.

Although FIGS. 1A and 1B illustrate an example of an electronic device 100 according to an embodiment of the current invention that has two field effect transistors, the general concepts of the current invention are not limited to this example. There could be additional electronic components in clued in the device 100, such as additional transistors, as well as resistors, diodes and/or capacitors, for example. In addition, one or more electronic device 100 could also be included as components in a circuit or other electronic device.

FIG. 3 is a schematic illustration of an electronic sensor 200 according to an embodiment of the current invention. The electronic sensor 200 includes a power source 202, a semiconductor component 204 electrically connected to the power source 202, an input electrode 208 electrically connected to the semiconductor component 204, and an output electrode 206 electrically connected to the semiconductor component 204. The semiconductor component 204 includes a semiconducting material. The electronic sensor 200 provides a first output voltage when a first input voltage has a value that is below a range of transition voltages, and a second output voltage when a second input voltage has a value that is above the range of transition voltages. The first output voltage is greater than the second output voltage. The semiconductor material is at least partially exposed such that a fluid of interest can be brought into contact with the semiconductor material to cause a change in the range of transition voltages. The semiconductor component can be, but is not limited to, two field effect transistors, similar to the embodiments of FIGS. 1A and 1B.

Figure 4:
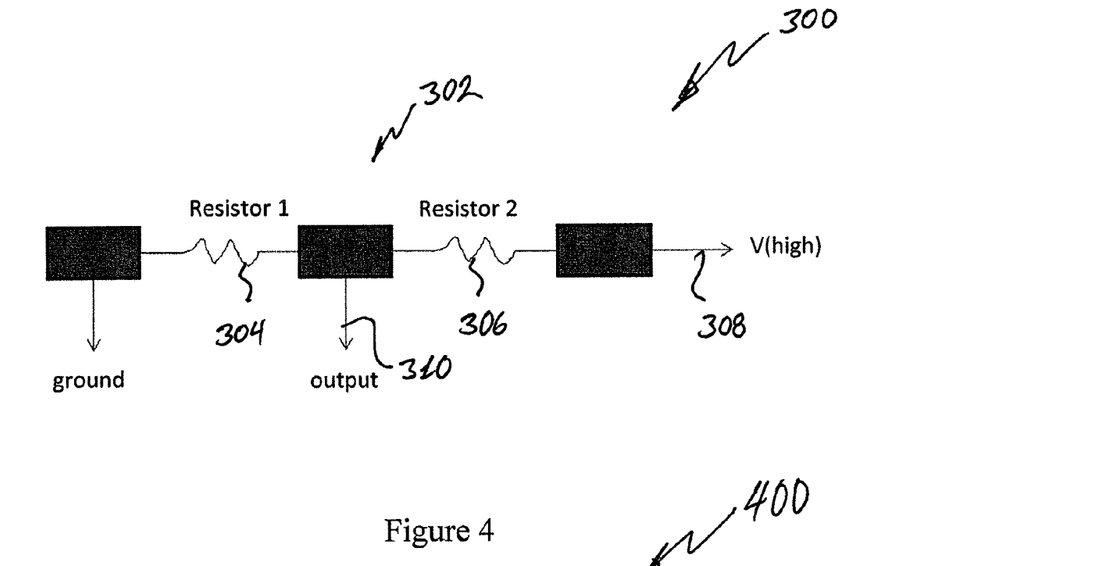
FIG. 4 is a schematic illustration of an electronic device according to another embodiment of the current invention.

FIG. 4 is a schematic illustration of an electronic circuit 300 for a fluid sensor according to another embodiment of the current invention. The electronic circuit 300 includes an electronic component 302 that includes a first material section 304 and a second material section 306. The electronic circuit 300 also includes an input electrode electrically connected to the electronic component 302, and an output electrode 310 electrically connected to the electronic component 302. Each of the first and second materials 304, 306 has a surface that can be exposed to a fluid. Each of the first and second materials 304, 306 changes an electrical property upon being exposed to the fluid to register a change in an output to the output electrode 310 indicative of a presence of the fluid. In the example of FIG. 4, the first and second materials 304, 306 correspond to respective first and second resistors. However, the general concepts of the current invention are not limited to this example. For example, first and second materials 304, 306 can be part of a respective resistor, diode, and/or transistor. Also, more than two materials can be included in the electronic component 302 according to other embodiments of the current invention.

In the example of FIG. 4, if resistor 1 has resistance R1 that is lower than R2 of resistor 2, then the output voltage will be "ground". If a fluid interacts with Resistor 1 and Resistor 2 such that R1 increases and R2 decreases, resulting in R2 being lower than R1, then the output voltage will be V(high). This is fundamentally the same as having the resistors be transistors, but not changing the input voltage during the process and, instead, monitoring the output voltage at a constant input voltage to observe a possible output voltage change because of the exposures. It is possible for the resistors to have transistor architecture, but where the effective input voltage on each transistor is pre-set by having applied static electrical polarization in or on an interface of the gate dielectric or by having a preset level of charge carriers as a consequence of chemical doping.

Figure 5:
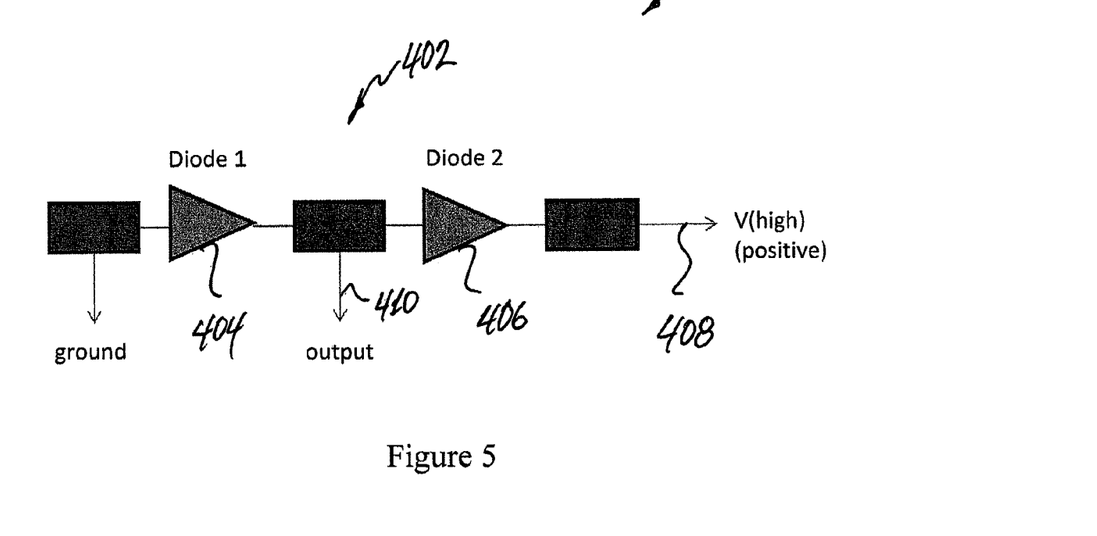
FIG. 5 is a schematic illustration of an electronic device according to another embodiment of the current invention.

FIG. 5 is a schematic illustration of an electronic circuit 400 for a fluid sensor according to another embodiment of the current invention. The electronic circuit 400 includes an electronic component 402 that includes a first material section 404 and a second material section 406. The electronic circuit 400 also includes an input electrode electrically connected to the electronic component 402, and an output electrode 410 electrically connected to the electronic component 402. Each of the first and second materials 404, 406 has a surface that can be exposed to a fluid. Each of the first and second materials 404, 406 changes an electrical property upon being exposed to the fluid to register a change in an output to the output electrode 410 indicative of a presence of the fluid. In the example of FIG. 5, the first and second materials 404, 406 correspond to respective first and second diodes.

As is shown in the FIG. 5, diodes 1 and 2 are both in reverse bias. As in the example of FIG. 4, if diode 1 has resistance R1 lower than R2 of diode 2, then the output voltage will be "ground". If a fluid interacts with diode 1 such that such that R1 increases, possibly because diode 1 is put more strongly into reverse bias or carriers in diode 1 are further depleted by the fluid, and/or R2 decreases, possibly because the pn junction of diode 2 is made less blocking to majority carriers, resulting in R2 being lower than R1, then the output voltage will be V(high).

EXAMPLES

Ammonia and Amines on P-Channel OFETs

Figure 6:
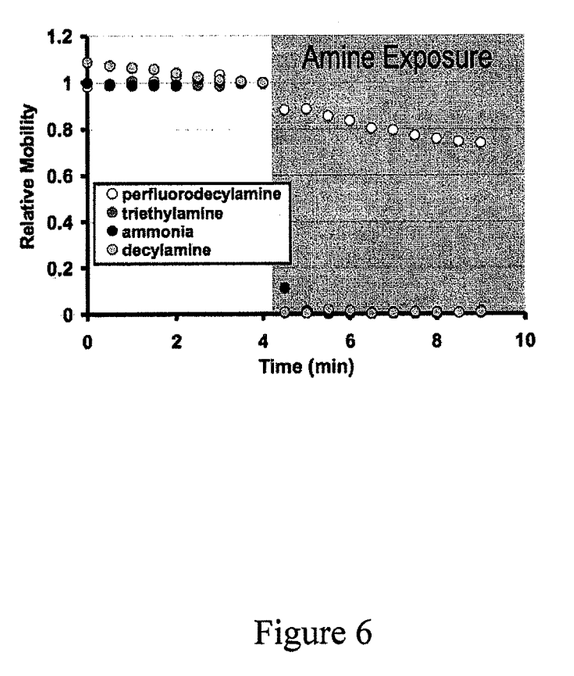
FIG. 6 is data showing relative mobility change upon exposure to various amines according to an embodiment of the current invention (relative mobility of PIF-TBT OFETs upon exposure to perfluorodecylamine, decylamine, triethylamine and ammonia). The major difference between the responses is the vapor pressure of the materials. Perfluorodecylamine is the only solid, thus having a low vapor pressure and a lower response.
Figure 7:
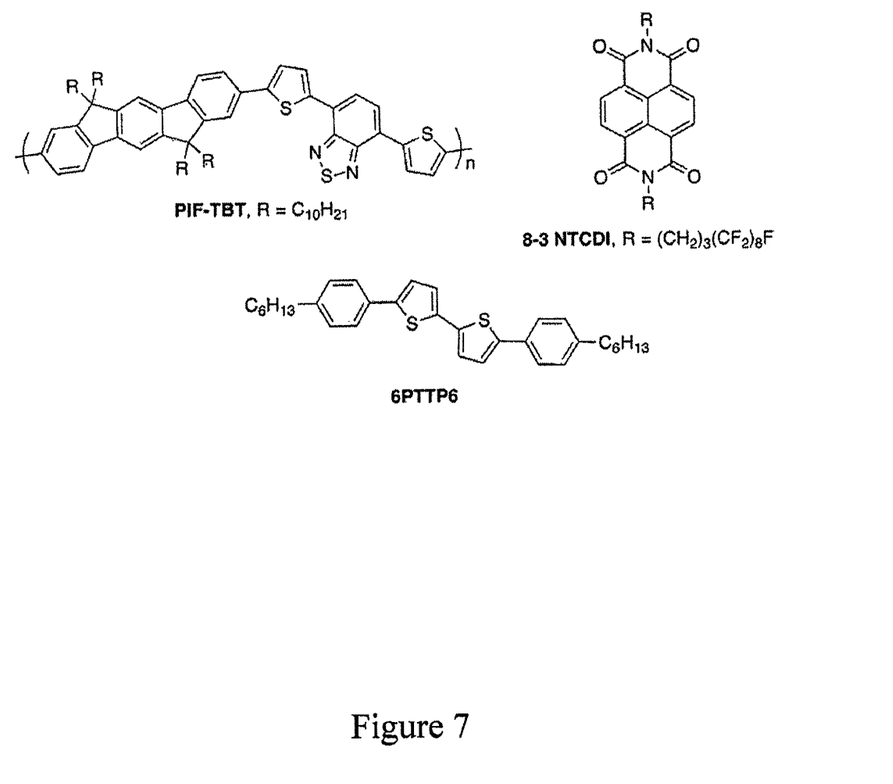
FIG. 7 shows molecular structures of some previously reported organic semiconductors.

The "current-lowering" or "resistance-increasing" effects of ammonia and trimethylamine (a source of "fish odor") have been known for p-type conducting polymers for over a decade (Bao Z, Dodabalapur A, Lovinger A J. *Appl. Phys. Lett.* 69, 4108 (1996); Assadi A Gustafsson G, Willander M, Svensson C, Inganäs O. *Synthetic Metals* 37, 123-130 (2009); Fiorido, T., Bendahan, M., Aguir, K. & Bernardini, S., Martini, C., Brisset, H., Fages, F., Videlot-Ackermann, C., Ackermann, 25. *Sensor. Actuat. B-Chem.* 151, 77-82 (2010)). The generally accepted mechanism is electron donation from the sp$^3$-hybridized nitrogen to the conducting polymer cation. This mechanism would be viable not only for ammonia but for any tertiary, secondary, or primary alkyl amine. FIG. 6 shows the effect of various amines on p-type metal-oxide-organic semiconductor (PMOS) devices. Upon exposure to amines, all of the PMOS devices display a decrease in current. Through further investigation, we find specifically that exposure both decreases carrier mobility and increases the threshold voltage of PMOS devices. We would expect any p-channel material (polymer or small molecule) to display this behavior, though to varying degrees. The resultant changes in current, mobility, and threshold voltage are reversible for very small concentrations over short periods of time. However, for substantial concentrations over longer periods of time, the changes are irreversible, most likely due to the high additional reactivity of the sp3-hybridized nitrogen in forming a covalent bond to the cationic site. Some of the materials used in this study are not commercially available (Zheng, Q., Jung, B. J., Sun, J. & Katz, H. E. *J. Amer. Chem. Soc.* 132, 5394-5404 (2010); Jung, B. J., Lee, K., Sun, J., Andreou, A. G., & Katz, H. E. *Adv. Funct. Mater.* 20, 2930-2944 (2010); Jung, B. J., Sun, J., Lee, T., Sarjeant, A., & Katz, H. E. *Chem. Mater.* 21, 94-101 (2009)); their structures are shown in FIG. 7.

Amines on N-Channel OFETs

Figure 8A:
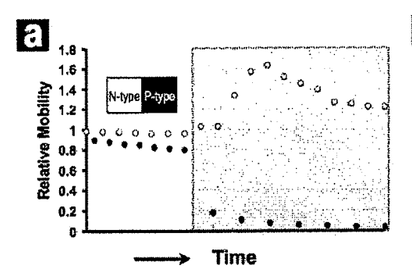
FIGS. 8A-8C show NMOS behavior compared to PMOS upon exposure to ammonia to explain concepts of some embodiments of the current invention.
Figure 8B:
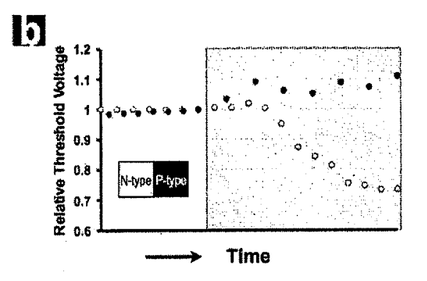
Figure 8C:
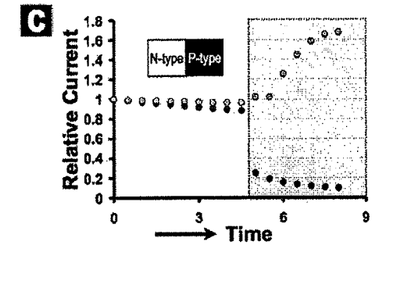

In addition to a PMOS, the CMOS inverter contains an n-type device (NMOS). In this example, we employ naphthalene tetracarboxylic diimides (NTCDIs), a class of n-channel semiconductors shown in previous work to be air-operable with highly-fluorinated side chains on the diimide nitrogens (Jung, B. J., Martinez-Hardigree, J. F., Dhar, B. M., Dawidczyk, T. J., Sun, J., See, K. C. & Katz, H. E. *ACS Nano* (2011), doi:10.1021/nn103115h; Jung, B. J., Tremblay, N. J., Yeh, M. L. & Katz, H. E. *Chem. Mater.* 23, 568-582 (2011), the entire contents of which are incorporated herein by reference). In contrast to PMOS devices, upon exposure of NMOS devices made with NTCDI to ammonia, the current increases, the mobility increases, and the threshold voltage decreases. This new behavior is shown in FIGS. 8A-8C. While the mechanism of this response is not precisely known, the interaction may proceed through an oxygen exclusion mechanism where amines help seal the grain boundaries of the film from the permeation of quenching oxygen. The mechanism may alternatively involve electron doping, or cancellation by ammonia of electron traps. Further investigation is required to determine which mechanism is the most likely. However, the increase in mobility tends to be partially reversed upon continued exposure to ammonia or amines for over 10-15 min. This indicates at least two operative interaction pathways may be at work. However, the concepts of the current invention are not limited to the correctness of theoretical models of the mechanisms responsible for the observed effects.

While numerous vapors have been shown to decrease currents in OFETs, it is very rare to find a class of chemicals that will increase such currents. In this way, the 'turn on' response of amine exposure to NMOS devices is very useful for excluding false positive responses.

CMOS Inverter Amine Sensors

There is a clear benefit to utilizing both the PMOS amine response as well as the NMOS response according to some embodiments of the current invention. Similar to the principle of the proposed 'electronic nose', a diversity of responses can give a greater selectivity for a particular analyte. In this case, the difference is substantial given that the responses are opposite in direction, and rather than separate them into distinct output channels, we combine them into a single synergistic one. One might consider this type of detection 'ratiometric' given that one can track a changing ratio between two independent responses. The simplest way to combine a PMOS and an NMOS device into a device with one input and one output is the CMOS inverter. Inverter behavior upon exposure to increasing concentrations of isopropylamine is shown in FIG. 9A.

The inverter switching voltage shifts to lower voltage due to the additive effect of the PMOS threshold voltage increasing and the NMOS threshold voltage decreasing and mobility increasing. Each concentration shows a gradient of responses toward lower voltage over time. Presumably, the incremental shifting within each concentration is due to an equilibration of the amine between the ambient air and within the OSC film.

Figure 9A:
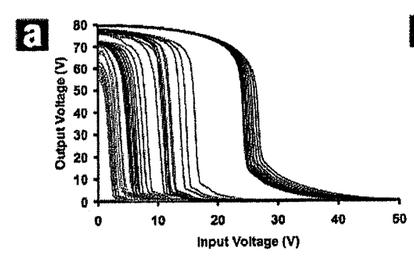
FIG. 9A is for a 6PTTP6/NTCDI inverter upon exposure.
Figure 9B:
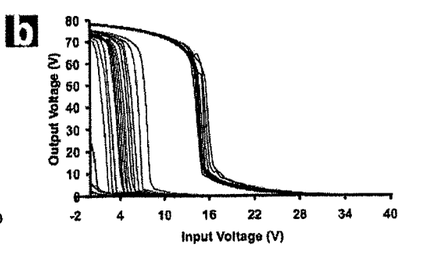
FIG. 9B is for exposing only the PMOS to amine.
Figure 9C:
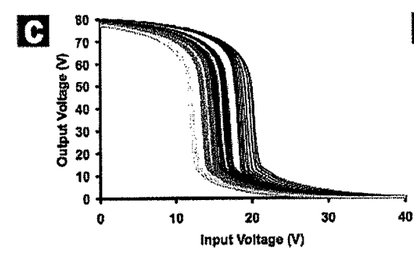
FIG. 9C is for exposing only the NMOS to amine.
Figure 9D:
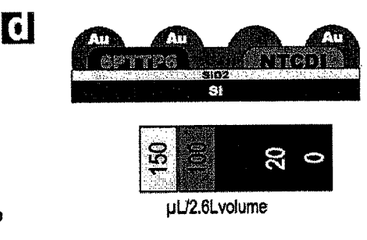
FIG. 9D is a schematic illustration of the device structure (top) and scale bars for exposure (bottom).
Figure 10:
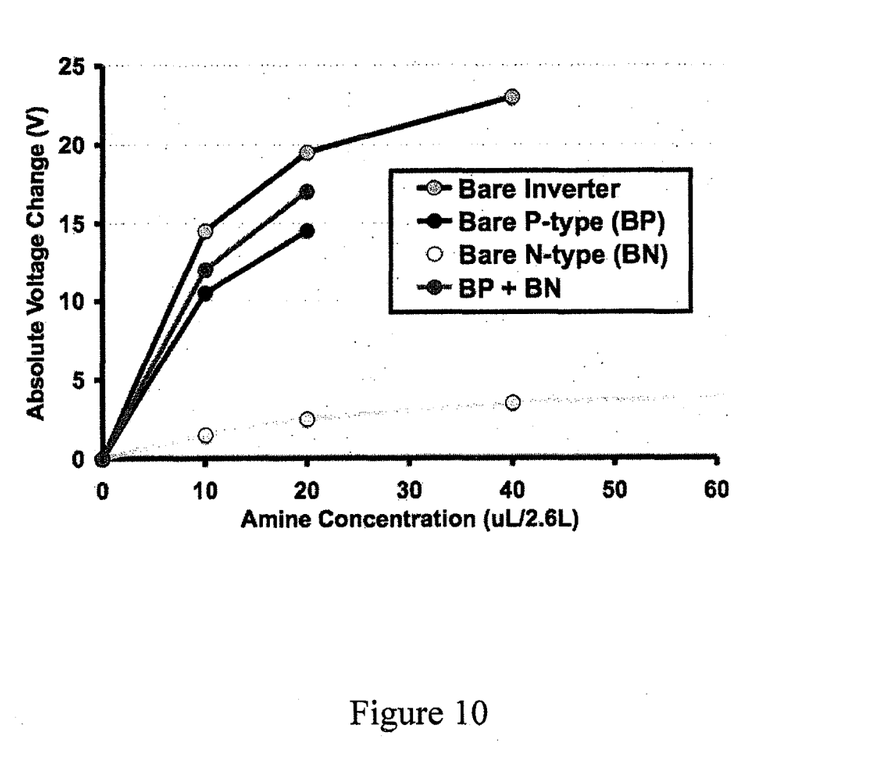
FIG. 10 is a graph showing the synergistic effect of CMOS inverter sensors according to an embodiment of the current invention.

To further highlight the cumulative nature of this response, a simple experiment is illustrated in FIGS. 9A-9D. Three identical inverters were made. In one, the NMOS device was isolated from the environment (FIG. 9B); in another, the PMOS device was isolated (FIG. 9C). The third inverter was left completely exposed (FIG. 9A). When the PMOS device is open to the environment, the increasing concentration of isopropylamine (chosen because of its boiling point slightly above room temperature, facilitating injection and complete evaporation) causes a series of incremental shifts in the switching voltage. In comparison, for the completely exposed device, small concentration changes cause larger stepwise jumps. The inverter where the NMOS device is left exposed and the PMOS is isolated is consistent with the behavior of the change in mobility of the NMOS upon exposure to amine. At first the switching voltage shifts dramatically to lower voltage. Upon further increase in concentration, the switching voltage reverses direction and backtracks to slightly a higher voltage. However, this voltage is still lower than the original starting point. At the smaller concentration values, the potential for a cumulative sensitivity of the CMOS inverter can be seen, as plotted in FIG. 10.

Figure 11A:
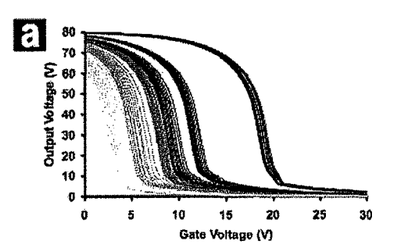
FIGS. 11A-11D provide data for an example of CMOS inverter sensor behavior for 8-3 NTCDI paired with various p-type materials; (a) CuPc/NTCDI inverter upon exposure, (b) Pentacene/NTDI, (c) 6PTTP6/NTCDI, and (d) scale bars of concentration.
Figure 11B:
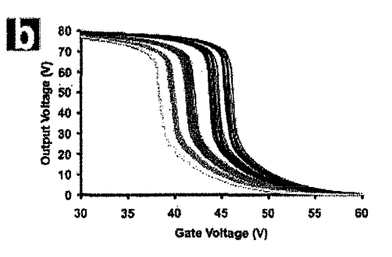
Figure 11C:
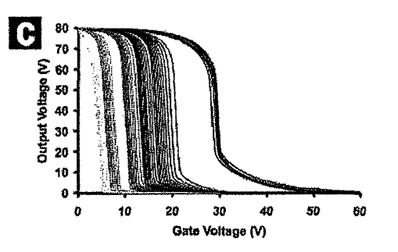
Figure 11D:
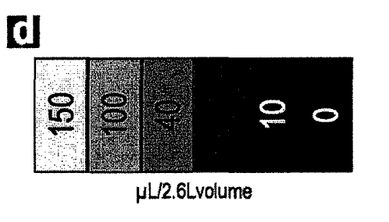

Sensitive inverters were also fabricated using different p-channel materials. FIGS. 11A-11D show the comparison between CMOS inverter sensor behavior with pentacene, copper(II) phthalocyanine (CuPc), and 6PTTP6 as the PMOS component. In this comparison, the NMOS components were identical. CuPc made low mobility, high threshold voltage transistors. The CuPc OFET sensitivity was also not very high. The inverter made from it had a very low switching voltage, even at high Vdd, due to the mismatch with the higher mobility and lower threshold voltage of the NMOS, and therefore displayed small absolute switching voltage shifts with increasing concentrations of isopropylamine (FIG. 11A). Pentacene PMOS devices had higher mobilities, better sensitivities, and the inverter made from it showed substantially larger shifts with increasing concentrations (FIG. 11B). However, the best CMOS inverter sensors were the ones made with 6PTTP6 (FIG. 11C). PMOS devices made from 6PTTP6 were much better matched with the NTCDI NMOS devices in terms of threshold voltage and mobility. A side-by-side comparison shows that the overall current levels of each OFET are within the same magnitude. A secondary indication of the similarity is in the 40V switching voltage, very close to the ideal 50V. These inverters produced very large shifts in switching voltage upon exposure to even small amounts of amine; the data sets within each concentration were completely separate with no overlap.

Additional Embodiments

Higher Order Logic from Inverter Sensors

A real benefit to the CMOS inverter sensor is the unambiguous 1 or 0. For example, if one chose to monitor at a constant output voltage just below the switching voltage of the inverter, any small concentration change would drop the signal below the monitoring voltage and the signal would go from a 1 to a 0. A series of these inverters could be arrayed together, each one being monitored at a different output voltage. As the concentration increased, different inverters would be triggered according to the sensitivity. The output would be a digital readout as a 0001 for a low concentration or a 1111 for a high concentration. This type of setup makes it easy to identify most false readings. For example, a readout of 1001 would not make any sense, and one would suspect that at least one of the inverters, the least sensitive one, would be faulty. Also, specificity is increased because the synergistic response would be less likely for an interferent than for an analyte intended for detection.

More sophisticated circuits can be made for the detection of combinations of analytes. If one has an inverter that is sensitive to ammonia and another that is sensitive to water, together one could obtain clear and simple answers to whether or not there is a certain amount of either analyte present. If the readout were 00 there would be no ammonia or water. If the readout were 01 or 10, there would either be a certain amount of ammonia or a certain amount of water. If the readout were 11, then the answer to the question, 'is there a certain amount of ammonia and a certain amount of water?' would be 'yes'. Other technological developments in the organic electronics community would be of additional use for sensors. For example, advances in inkjet printing technology and threshold voltage tuning by the printing of charged dielectrics (Dhar, B. M., Özgün, R., Dawidczyk, T., Andreou, A. & Katz, H. E. Mater. Sci. Eng. R (2010), doi:10.1016/j.mser.2010.11.001) can provide high throughput production of organic-based digital sensors and their integration with organic memory transistors (Jung, B. J., Tremblay, N. J., Yeh, M. L. & Katz, H. E. *Chem. Mater.* 23, 568-582 (2011)) and silicon signal processors according to an embodiment of the current invention.

Methods

Device Fabrication.

All CMOS inverter sensors were fabricated and characterized using standard methods. All materials were purchased from Sigma-Aldrich unless synthesized or otherwise denoted. Highly n-doped <100> silicon wafers with a 300 nm thermally grown oxide were diced into 1 in. by 1 in. substrates. The wafers were cleaned by sonication in acetone and isopropanol, and then dried by forced nitrogen gas. Substrates were dried more thoroughly via 100° C. vacuum annealing for 20 min prior to a 2-hour exposure to hexamethyldisilazane (HMDS) vapor at 100° C. in a loosely sealed vessel. Individual sensitive transistors were fabricated via spin-coating (PIF-TBT, 7 mg/mL in chlorobenzene, 1.5 k spin speed) or thermally evaporating (8-3NTDCI, substrate temperature held at 100° C.) the OSC directly onto HMDS substrates, followed by thermally evaporated gold electrodes (50 nm) through a shadow mask. CMOS inverters were fabricated by thermal evaporation of OSCs onto HMDS substrates, to a thickness of 30 nm, that were first spun-coat with a thin film of poly(alpha-methylstyrene) (5 mg/mL of toluene, 2 k spin speed). High-grade pentacene and CuPc were used as-is from Sigma-Aldrich. 8-3NTCDI (Zheng, Q., Jung, B. J., Sun, J. & Katz, H. E. J. *Amer. Chem. Soc.* 132, 5394-5404 (2010), the entire contents of which is incorporated herein by reference) and 6PTTP6 (Jung, B. J., Sun, J., Lee, T., Sarjeant, A., & Katz, H. E. *Chem. Mater.* 21, 94-101 (2009)) were synthesized according to literature procedure and triply sublimed for purity. 8-3NTCDI was evaporated through a shadow mask at a substrate temperature of 100° C. before the p-type material was evaporated onto the same substrate through a different shadow mask. Gold electrodes were evaporated through a shadow mask to the thickness of 60-75 nm.

Electrical Measurements.

Individual sensitive transistors were measured using an Agilent 4155C semiconductor analyzer in air. CMOS inverter sensors were measured in a four-probe vacuum probe station (Janis Research) with a calculated internal volume of 2.6 L attached to a Keithley 4200 semiconductor characterization system.

Figure 12:
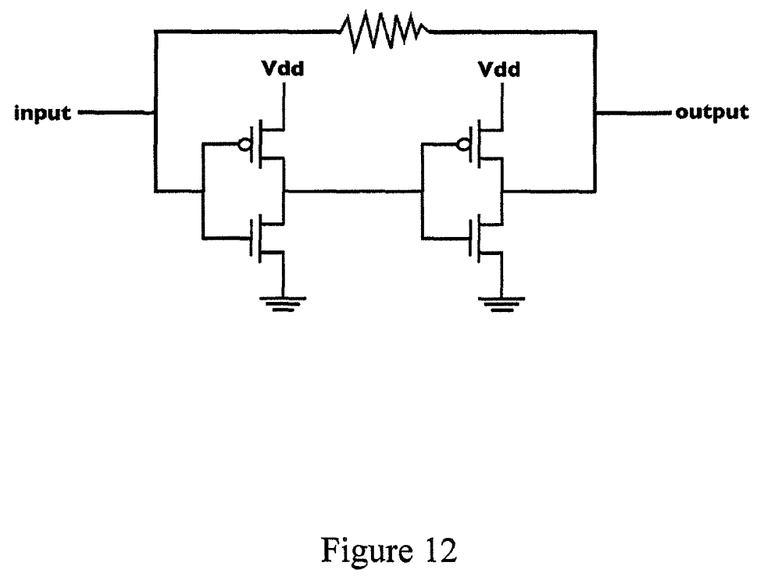
FIG. 12 is a schematic of an electronic device according to another embodiment of the current invention.

In some embodiments, inverter sensors, along with other transistors, can be incorporated into logic and circuit components with higher complexity. For example, two inverters can be wired together to make a simple bistable circuit, as shown in FIG. 12. In this case, the output is amplified, stabilized, and digitized. Similarly, sensitive inverters can be incorporated into ring oscillators for ease of measurement, as well as an amplified signal. Any device architecture including, but not limited to: inverters, amplifiers, comparators, ring oscillators, NOT gates, NOR gates, NAND gates, XOR gates, AND gates, other logic gates can provide more sensitive and/or more selective sensors when sensitive transistors with synergistic responses are used according to embodiments of the current invention. Additional benefits to using the aforementioned architectures can include a stabilized output signal and the possibility for a direct digital readout.

The concept of using higher order structures to afford higher quality electronic sensors according to some embodiments of the current invention can be used to make all types of organic-based sensors. Examples described could be used for ammonia sensors, general amine sensors, and sensors for particular amines, for example. Also some embodiments of the current invention could be used for TNT sensors, DNT sensors, dihydrogen sulfide sensors, water sensors, particle sensors, as well as any other analyte that could be detected by an organic material in a transistor setting.

The embodiments illustrated and discussed in this specification are intended only to teach those skilled in the art to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. An electronic analyte detection device, comprising:
   a first field effect transistor comprising a first gate electrode, a first drain electrode, and a first source electrode;
   a second field effect transistor comprising a second gate electrode, a second drain electrode, and a second source electrode, said first and second gate electrodes being integral, and said first and second source electrodes being integral;
   an input electrode electrically connected to said first and second gate electrodes;
   an output electrode electrically connected to said first and second source electrodes, and
   a processor electrically connected to the output electrode configured to determine at least a presence of an analyte of interest;
   wherein said first field effect transistor further comprises a first semiconductor material, said first semiconductor material is a p-type semiconductor material or a n-type semiconductor material,
   wherein said second field effect transistor further comprises a second semiconductor material, said second semiconductor material is a p-type semiconductor material or a n-type semiconductor material,
   wherein each of said first semiconductor material and second semiconductor material has a surface configured to be exposed to a fluid,
   wherein each of said first semiconductor material and second semiconductor material changes an electrical property thereof to detect the analyte of interest while being exposed to said fluid when said analyte of interest is present in said fluid, and
   wherein said n-type semiconductor material comprises naphthalene tetracarboxylic diimide (NTCDI) and said p-type semiconductor material comprises pentacene, copper(II) phthalocyanine (CuPc), or 6PTTP6.

2. The electronic analyte detection device according to claim 1, wherein each of said first semiconductor material and said second semiconductor material changes an electrical property while being exposed to said fluid synergistically to enhance an effect of exposure of said fluid on said electronic device.

3. The electronic analyte detection device according to claim 1, wherein said first semiconductor material at least one of decreases carrier mobility or increases a threshold voltage upon being exposed to said fluid.

4. The electronic analyte detection device according to claim 3, wherein said second semiconductor material at least one of increases carrier mobility or decreases a threshold voltage upon being exposed to said fluid.

5. The electronic analyte detection device according to claim 1, wherein said fluid is at least one of a gas or a vapor.

6. The electronic analyte detection device according to claim 1, wherein said fluid is at least one of a liquid, a suspension or an emulsion.

7. The electronic analyte detection device according to claim 1, wherein said fluid comprises at least one of ammonia, an amine, aza-aromatic compound with pKa>4; dihydrogen sulfide, a compound with an acidic proton or a Lewis acidic functionality, or an organic thiol.

8. The electronic analyte detection device according to claim 1, wherein the naphthalene tetracarboxylic diimide (NTCDI) consists of 8-3NTCDI.

9. The electronic analyte detection device according to claim 1, wherein the first semiconductor material is a p-type semiconductor material comprising 6PTTP6 and the second semiconductor material is a n-type semiconductor material comprising NTCDI.

10. An electronic sensor, comprising:
a power source;
a semiconductor component electrically connected to said power source, said semiconductor component comprising a first semiconducting material and a second semiconducting material, said first semiconductor material is a p-type semiconductor material or a n-type semiconductor material, and said second semiconductor material is a p-type semiconductor material or a n-type semiconductor material;
an input electrode electrically connected to said semiconductor component;
an output electrode electrically connected to said semiconductor component, and
a processor electrically connected to the output electrode configured to determine at least a presence of a fluid;
wherein said electronic sensor provides a first output voltage when a first input voltage has a value that is below a range of transition voltages,
wherein said electronic sensor provides a second output voltage when a second input voltage has a value that is above said range of transition voltages,
wherein said first output voltage is greater than said second output voltage, wherein said first and second semiconductor materials are at least partially exposed such that the fluid of interest is brought into contact with said first and second semiconductor material to cause a change in said range of transition voltages, and
wherein said n-type semiconductor material comprises naphthalene tetracarboxylic diimide (NTCDI) and said p-type semiconductor material comprises pentacene, copper(II) phthalocyanine (CuPc), or 6PTTP6.

11. The electronic sensor of claim 10, wherein said changes in said range of transition voltages of said first semiconducting material and said second semiconducting material are synergistic when exposed to said fluid to enhance said change in said range of transition voltages.

12. An electronic analyte detection circuit comprising a plurality of electrically connected electronic components, wherein at least one of said plurality of electrically connected electronic components is an inverter comprising:

a first field effect transistor comprising a first gate electrode, a first drain electrode, and a first source electrode;
a second field effect transistor comprising a second gate electrode, a second drain electrode, and a second source electrode, said first and second gate electrodes being integral, and said first and second source electrodes being integral;
an input electrode electrically connected to said first and second gate electrodes;
an output electrode electrically connected to said first and second source electrodes, and
a processor electrically connected to the output electrode configured to determine at least a presence of a fluid;
wherein said first field effect transistor further comprises a first semiconductor material, said first semiconductor material is a p-type semiconductor material or a n-type semiconductor material,
wherein said second field effect transistor further comprises a second semiconductor material, said second semiconductor material is a p-type semiconductor material or a n-type semiconductor material,
wherein said first semiconductor material and second semiconductor material has a surface that is configured to be exposed to the fluid,
wherein said at least one of said first semiconductor material and second semiconductor material changes an electrical property thereof while being exposed to said fluid, and
wherein said n-type semiconductor material comprises naphthalene tetracarboxylic diimide (NTCDI) and said p-type semiconductor material comprises pentacene, copper(II) phthalocyanine (CuPc), or 6PTTP6.

13. An electronic circuit for a fluid sensor, comprising:
an electronic component comprising a first material section and a second material section, said first material section is a p-type semiconductor material or a n-type semiconductor material, and said second material section is a p-type semiconductor material or a n-type semiconductor material;
an input electrode electrically connected to said electronic component;
an output electrode electrically connected to said electronic component, and
a processor electrically connected to the output electrode configured to determine at least a presence of an analyte of interest;
wherein each of said first and second material sections have a surface configured to be exposed to a fluid,
wherein each of said first and second material sections change an electrical property upon being exposed to said fluid to register a change in an output to said output electrode when the analyte of interest is present in said fluid, and
wherein said n-type semiconductor material comprises naphthalene tetracarboxylic diimide (NTCDI) and said p-type semiconductor material comprises pentacene, copper(II) phthalocyanine (CuPc), or 6PTTP6.

* * * * *